US007090653B2

(12) United States Patent
Moeller

(10) Patent No.: US 7,090,653 B2
(45) Date of Patent: Aug. 15, 2006

(54) CERVICAL COLLAR WITH CURVE INDUCING TAB

(75) Inventor: David Moeller, Tustin, CA (US)

(73) Assignee: CARSAR, LLC, Seal Beach, CA (US)

( * ) Notice: Subject to any disclaimer, the term of this patent is extended or adjusted under 35 U.S.C. 154(b) by 0 days.

(21) Appl. No.: 10/938,316

(22) Filed: Sep. 10, 2004

(65) Prior Publication Data

US 2006/0058718 A1    Mar. 16, 2006

(51) Int. Cl.
*A61F 5/00* (2006.01)

(52) U.S. Cl. .............................. 602/18; 602/17; 2/468; 128/DIG. 23

(58) Field of Classification Search .................. 602/12, 602/17, 18; 2/468; 128/97.1, 869, DIG. 23
See application file for complete search history.

(56) References Cited

U.S. PATENT DOCUMENTS

| | | | | | |
|---|---|---|---|---|---|
| 2,791,999 | A | * | 5/1957 | Bustamante | 601/39 |
| 3,285,243 | A | * | 11/1966 | Yellin | 602/18 |
| 3,756,226 | A | * | 9/1973 | Calabrese et al. | 602/18 |
| 4,854,306 | A | * | 8/1989 | Pujals, Jr. | 602/18 |
| 4,886,052 | A | * | 12/1989 | Calabrese | 602/18 |
| 5,038,759 | A | | 8/1991 | Morgenstern | |
| 5,097,824 | A | | 3/1992 | Garth | |
| 5,230,698 | A | | 7/1993 | Garth | |
| RE34,714 | E | * | 8/1994 | Burns et al. | 602/18 |
| 5,437,612 | A | | 8/1995 | Moore et al. | |
| 5,688,229 | A | * | 11/1997 | Bauer | 602/18 |
| 5,776,088 | A | | 7/1998 | Sereboff | |
| 5,964,722 | A | * | 10/1999 | Goralnik et al. | 602/18 |
| 5,976,098 | A | | 11/1999 | Sereboff | |
| 6,071,255 | A | * | 6/2000 | Calabrese | 602/18 |
| 6,254,560 | B1 | * | 7/2001 | Tweardy et al. | 602/18 |
| 6,315,746 | B1 | * | 11/2001 | Garth et al. | 602/18 |
| 6,423,020 | B1 | * | 7/2002 | Koledin | 602/18 |
| 6,494,854 | B1 | * | 12/2002 | Visness et al. | 602/18 |
| 6,872,188 | B1 | * | 3/2005 | Caille et al. | 602/18 |
| 2003/0060744 | A1 | * | 3/2003 | Caille et al. | 602/18 |
| 2003/0181838 | A1 | * | 9/2003 | Garth | 602/18 |
| 2005/0101896 | A1 | * | 5/2005 | Calabrese | 602/18 |

* cited by examiner

*Primary Examiner*—Henry Bennett
*Assistant Examiner*—Amanda Wieker
(74) *Attorney, Agent, or Firm*—Rutan & Tucker LLP

(57) ABSTRACT

A cervical collar has a back panel coupled to a movable element to provide adjustable pressure to the back of a wearer's neck, to thereby assist adoption of a proper cervical curvature.

19 Claims, 1 Drawing Sheet

CERVICAL COLLAR WITH CURVE INDUCING TAB

FIELD OF THE INVENTION

The field of the invention is cervical collars.

BACKGROUND

It is well known to use cervical collars to partially immobilize the cervical spine. The simplest such collar is essentially a cylinder that fits around the neck. Such devices are often problematic for many reasons, including discomfort to the wearer, and improper support for the occiput and chin. They are also problematic because they can improperly reduce the lordotic curve of the cervical spine.

To improve comfort and adjustability of cylindrical cervical collars, the collar height can be reduced and head support provided using support pads that are coupled to the collar via support posts as described in U.S. Pat. Nos. 5,776,088 and 5,976,098 to Sereboff. While such collars can be configured to match various anatomical shapes, several problems remain. Among other things, the force distribution of the support pads is typically restricted to the area in which the support posts are attached to the collar. Thus, head stability can not be entirely assured under all circumstances. Furthermore, Sereboff's collars fail to promote proper cervical curvature as the support pads are aligned with the occipital portion of the skull.

Alternatively, as described in U.S. Pat. No. 5,437,612 to Moore et al. or U.S. Pat. No. 5,038,759 to Morgenstern, a cervical collar includes a posterior portion that is contoured to follow the curve of the back of the head or occiput to support the head. Such configurations advantageously tend to distribute forces from the head to the collar over a relatively large contact area. Moreover, a contoured posterior portion typically helps restrain rotational movement. However, while the posterior portion of at least some of these collars are adjustable in width and angle relative to the anterior portions, the posterior portion fails to promote or maintain proper cervical curvature. Similarly, Applegate et al. teach in U.S. Pat. No. 3,313,297 a cervical splint in which the head angle is movably adjusted using a chin support that is adjustably coupled to a collar.

In still further known cervical collars, as described in U.S. Pat. Nos. 5,097,824 and 5,230,698 to Garth, a cervical collar has a posterior portion that circumferentially supports the occipital portion of a skull, and further includes an occipital shelf to provide additional supports. The shelf in such collars can be formed by the back portion of the collar, or an angled element can be inserted for additional support. While such collars can provide at least some degree of assistance for proper cervical curvature, various difficulties nevertheless remain. Among other things, achieving the desired curvature of the supporting structure requires a "2nd step" once the collar has been properly tightened.

Thus, while numerous cervical collars are known in the art, all or almost all of them suffer from one or more disadvantages. Consequently, there is still a need to provide improved cervical collars, and especially collars that promote or assist proper cervical curvature.

SUMMARY OF THE INVENTION

The present invention is directed to configurations and methods of cervical collars, and especially to those that promote a desirable cervical curvature. Particularly preferred cervical collars include a back panel with a top and a bottom, and a tab located intermediately between the top and the bottom. Most preferably, the tab is configured to adjustably extend anteriorly to press against a posterior portion of the wearer's neck.

In further preferred aspects, the back panel is fully removable from other portions of the collar and can lie substantially flat. Contemplated collars can further include a strap that couples with the tab and that can be pulled to increase pressure of the tab against the wearer's neck. In such devices, a stop mechanism can be included that restricts the strap from moving back and forth across the tab. Particularly preferred collars include a padding (e.g., foam) between the tab (e.g., plastic) and the wearer's neck, and the tab is continuous with a support member that restricts extension of the wearer's head. In such devices, the strap passes through holes in the support member (e.g., plastic).

Additionally, or alternatively, contemplated devices include a strap that couples with the tab and that can be pulled to increase the pressure of the tab against the wearer's neck, a padding between the tab and the wearer's neck, and wherein the tab is continuous with a support member that restricts extension of the wearer's head. Preferably, the strap in such collars passes through holes in both the padding and the support member. Where desirable, contemplated collars also include a front piece that rests on the wearer's chest, and a chin support, and wherein the strap is removably attachable to at least one of the front piece and chin support (e.g., using a hook and loop fastener).

Various objects, features, aspects and advantages of the present invention will become more apparent from the following detailed description of preferred embodiments of the invention, along with the accompanying drawings in which like numerals represent like components.

DETAILED DESCRIPTION

Figure 1:
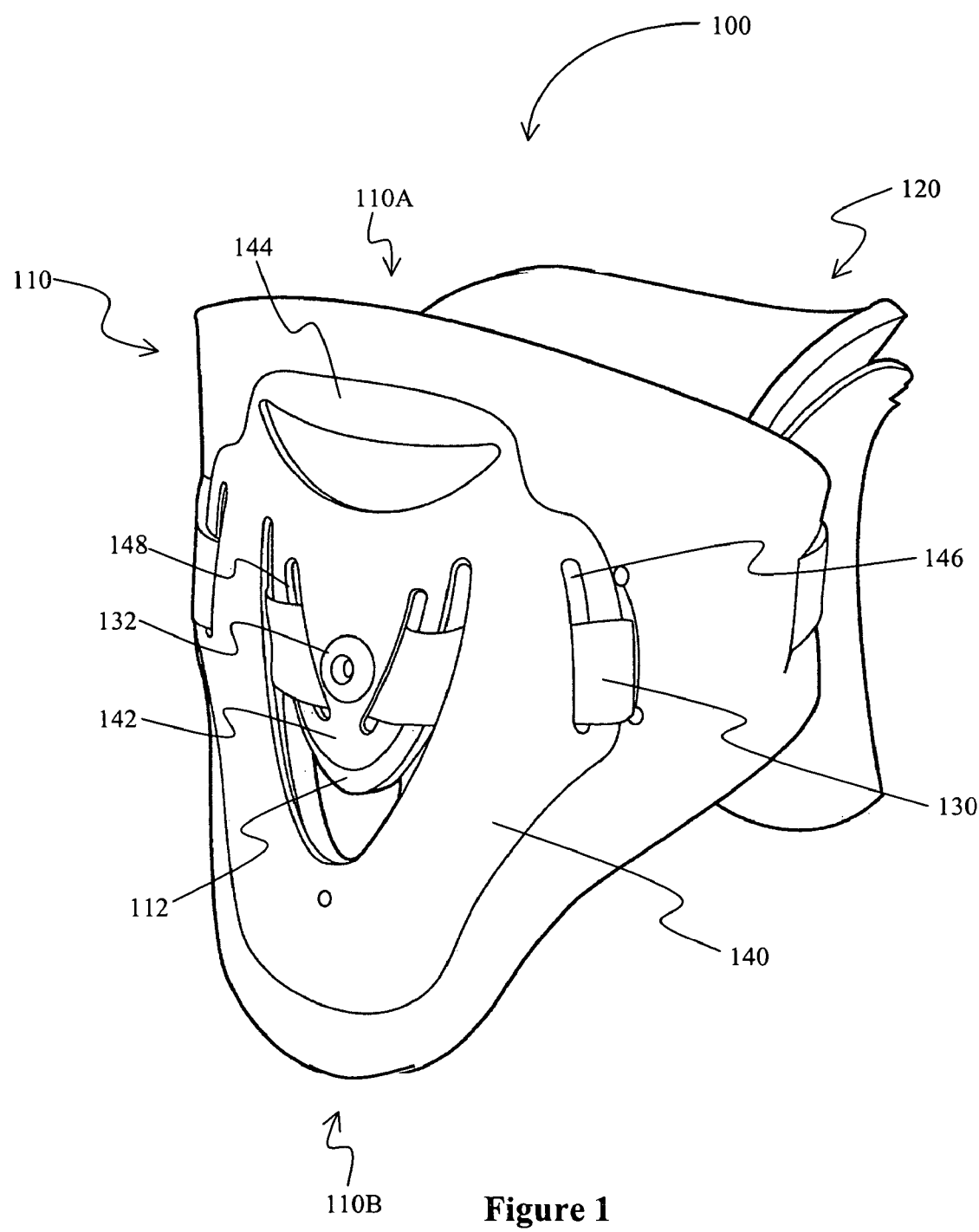
FIG. 1 is schematic perspective view of an exemplary cervical collar according to the inventive subject matter.

The inventor has discovered that a cervical collar can be manufactured that not only provides stable support for head and neck but also promotes desirable cervical lordosis (i.e., cervical anterior curvature considered clinically normal). Most preferably, a front piece in such collars is coupled to a back panel that includes a tab (or other movable element), wherein the tab is adjustably coupled to the back panel such that the tab promotes the desired cervical curvature. The position of the tab can be changed in numerous manners. However, it is preferred that the position of the tab is adjusted using a strap, and most preferably using the same strap that couples the back panel to the front piece.

In one especially preferred aspect of the inventive subject matter, a cervical collar that can be positioned about a wearer's neck includes a back panel to which a tab is coupled (e.g., in a position intermediate between top and bottom of the back panel), wherein the tab extends anteriorly to press against a posterior portion of the wearer's neck to thereby promote a cervical curvature.

In FIG. 1, an exemplary cervical collar according to the inventive subject matter is depicted. Here, collar 100 has a back panel 110 that is coupled to a front piece 120 via hook and loop fasteners that are attached to the ends of the strap 130 (the ends of the strap couple to the sides of the front piece, respectively). The front piece 120 has an upper portion that receives the chin of a user (not shown) while the lower portion engages with the sternum or upper area of the chest of the user.

Back panel 110 typically includes an opening between the top 110A and the bottom 110B, wherein the tab 112 of the back panel is located in the opening, and wherein the tab is most preferably continuous with the remainder of the back panel. The support member 140 is preferably coupled to the back panel 110 via one or more rivets 132, wherein the support member 140 includes a support tab 142 that at least partially overlaps with the tab 112 of the back panel. In especially preferred aspects, strap 130 is fixedly coupled to the support tab 142 and tab 112 via a stop mechanism (most preferably a rivet), and further threaded through openings 148 and 146 of the support tab 142 and support member 140 such that when the back panel is in use, pulling on the strap will move the tab and support tab anteriorly to thereby promote a cervical curvature. The top 144 of the support member further includes a restrictor element that restricts extension of the wearer's head while the bottom of the support member cooperates with the bottom 110B of the back panel to transmit forces from the head to the back and shoulder of the person wearing the collar.

In other preferred aspects of the inventive subject matter, the back panel is configured to be entirely disconnected from the front piece when the collar is not in use. This reduces manufacturing and shipping costs. Most preferably, the back panel is fabricated from a substantially flat and soft foam material that can be bent to conform with a person's back and neck when the collar is worn. The term "substantially flat" as used herein means that the absolute distance between the highest and lowest point on the surface to which the support member is coupled is less than 3 cm, more typically less than 2 cm and most typically less than 1 cm. Alternatively, however, it is contemplated that any suitable material can be used, as long as it can be formed into a back panel and retain a desired shape. Suitable materials include, for example, natural and synthetic polymers, carbon-reinforced materials, metals and metal alloys, and all reasonable combinations thereof (e.g., metal wire-reinforced soft polymer).

In still other preferred aspects, and especially where no support member is coupled to the back panel (e.g., support member can be formed as an integral part of the back panel), the tab in the back panel can be coupled to a strap such that pressure of the tab against the wearer's neck increases when the strap is pulled. For example, the back panel and the tab can have openings through which the strap is threaded in a similar manner as depicted in FIG. 1. Therefore, it should be recognized that the desired cervical curvature can be continuously adjusted using the strap by forcing the tab anteriorly when the back panel is in a curved configuration. Most preferably, the strap is fixedly coupled to the tab and/or back panel to prevent the strap from moving back and forth across the tab.

Alternatively, or additionally, contemplated back panels can also include a support member that is fixedly (or in some instances movably) coupled to the back panel. Such support members are especially advantageous where the back panel is more pliable than the support member. For example, where the back panel comprises a relatively soft foam, a preferred material for the support member is a hard plastic (e.g., polyethylene, polystyrene, etc.). In such collars, it is generally preferred that the upper portion of the support member comprises an element that restricts extension of the wearer's head.

It is further preferred that the support tab and/or the element that restricts extension of the wearer's head are continuous with the support element (e.g., integral with the support element), however, discontinuous coupling is also contemplated. For example, where it is desired that the restriction element is adjustable in height, the restriction element can be coupled to the support member via a bracket, or other adjustable coupling. Similarly, it should be recognized that the tab and/or supporting tab can be continuous with the back panel and/or supporting element, or that the tab and/or supporting tab can be coupled to the back panel and/or supporting element in a discontinuous fashion. For example, the tab and/or supporting tab can be exchangeable soft blocks of varying shape corresponding at least partially to the cervical spine that are removably coupled to the strap (or other component of the collar).

Where the collar includes a supporting member, it is further preferred that a strap is threaded through one or more openings of the support member (and/or support tab) to allow coupling of the front portion to the back panel and to further allow adjustment of the support tab and tab relative to the neck of a person wearing the collar. Most preferably, the strap is coupled to the support tab and configured such that a pressure of the tab of the back panel against the wearer's neck increases when the strap is pulled.

Alternatively, it should be recognized that the tab can be continuously moved towards the wearer's neck using various configurations other than a strap threaded through the support member. For example, a wedge or screw mechanism can be coupled to the back panel and/or supporting member to force the tab and/or supporting tab against a person's neck. With respect to the tab, it is generally preferred that the tab has a flat configuration and is fabricated from the same material as the back panel. However, in alternative aspects of the inventive subject matter, the tab can be shaped to conform to a particularly desired cervical curvature, and/or to conform to at least one side of the neck towards the anterior.

Furthermore, it is contemplated the particular nature of the front piece is not limited to the inventive subject matter, and all known front pieces are deemed suitable for use herein so long as such front pieces will cooperate with the back panel to form a cervical collar. With respect to the coupling of the front piece to the back panel, it is generally preferred that the strap will be used not only to continuously adjust the position of the tab/support tab, but also to removably affix the front piece to the back panel. However, where desired, the back panel can also be coupled to the front piece using connectors other than the strap, and suitable connectors include snaps, buttons, rails, etc.

EXAMPLE

In one exemplary cervical collar following the general structure of the device depicted in FIG. 1, the collar includes a back panel comprising a sheet of flexible polymer composite material with a padding layer, preferably a foam polymer layer. The back panel is typically configured to extend around the back of the neck of a patient. Extending forward from the back panel on each side is a flexible attachment band (using hook and loop type fastener components) for securing the back panel to the front piece.

One portion of the front piece is preferably formed from a sheet of flexible synthetic polymer composite material that engages from the sides of the neck of the patient down over his chest. The back edges of the front piece lie approximately in the plane of the cervical spine. From the back edge, the front piece extends forward and sweeps down to form an upper edge, which is sufficiently far down on the chest to define a tracheotomy access opening at the front of the patient's neck. The lower edge of the front piece has tabs thereon. The tabs have notches between and openings therein to provide a progressively smaller cross section from the free lower edge of the solid portion of the front piece. The tabs provide an easier transition between the constraining effect of the collar and the unsupported surface adjacent thereto. In order to strengthen the front piece, a strengthener is attached via rivets to the front piece and is preferably formed in a U-shaped structure (material is preferably sheet synthetic polymer composite material). The back end of the strengthener is also attached to the front piece via rivets. Similar attachment is provided at the opposite side.

A padding layer is coupled to that portion of the front piece and is preferably a layer of synthetic foam material having fabric attached to each side. The inside fabric layer is suitable for engagement against the patient, while the outside fabric layer on the foam padding layer is suitable to be engaged by the hook portion of a hook-and-loop fastener. The padding layer extends up and back along the interior of the front piece and terminates in an ear, which extends back beyond the back ends of the front piece.

The other portion of the front piece is the chin piece, which is preferably formed of a flexible sheet synthetic polymer material and is configured so that the chin-supporting section extends forward. The chin piece is typically attached to the other portion of the front piece by two rivets on each side, preferably hidden under the hook fastener band. It should be noted that the entire center section of the chin piece in the forward direction is unsupported, and it is preferred that support for the chin at the center of the chin piece is provided by the stiffness of the chin piece. The chin piece is preferably cut from flexible sheet polymer material so that it is bendable to the patient's chin contours, but sufficiently stiff to provide adequate support.

It is further preferred that a padding layer (e.g., foam padding layer with a suitable fabric on the inside surface for skin contact) covers the inside of the chin piece. The outside of the padding layer is covered with a fabric which can be engaged by the hook portion of a hook-and-loop fastener system. In a preferred manner of attachment, the hook and loop fastener is attached to the front piece, engages via an opening with the back panel, and loops back to the front piece for closure.

In use, the front piece of the cervical collar is placed against the chest of a user with the chin piece positioned under the chin of the patient. The back panel is placed behind the neck of the patient and overlaps the outside of the front piece on both sides. The front piece is thrust back at the same time the back panel is thrust forward. The attachment bands on the back panel are pulled forward and affixed to the corresponding bands on the front piece. Mounting of the collar to the patient should be sufficiently firm so that the tab on the back is resiliently bent. This applies resilient stabilization to the cervical spine and head of the patient.

Thus, specific embodiments and applications of cervical collars with curve inducing tabs have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced.

What is claimed is:

1. A cervical collar that can be positioned about a wearer's neck, comprising:
    a back panel having a top and a bottom;
    a tab located intermediate between the top and the bottom, and operating substantially independently of the panel to press against a posterior portion of the wearer's neck to thereby promote a cervical curvature;
    a front panel; and
    a connecting strap that couples the front and back panel, wherein the strap overlaps a portion of the tab.

2. The collar of claim 1 wherein the back panel is fully removable from other portions of the collar, and can lie substantially flat.

3. The collar of claim 1, wherein the strap is coupled to the tab and is configured such that a pressure of the tab against the wearer's neck increases when the strap is pulled.

4. The collar of claim 3, further comprising a stop mechanism that restricts the strap from moving back and forth across the tab.

5. The collar of claim 4 wherein at least part of the tab is formed from the back panel.

6. The collar of claim 1, further comprising a support member coupled to the back panel, wherein the support member has a support tab that coincides at least partially with the tab of the back panel.

7. The collar of claim 6 wherein the tab is continuous with the back panel.

8. The collar of claim 6 wherein the back panel comprises a foam and the support tab comprises a plastic.

9. The collar of claim 6 wherein the support member includes an element that restricts extension of the wearer's head.

10. The collar of claim 9 wherein the support tab is continuous with the element that restricts extension of the wearer's head.

11. The collar of claim 6, further comprising a strap coupled to the support tab and configured such that a pressure of the tab of the back panel against the wearer's neck increases when the strap is pulled.

12. The collar of claim 11 wherein the strap passes through holes in the support member.

13. The collar of claim 12 wherein the strap passes through holes in the support tab.

14. The collar of claim 11, further comprising a front piece that rests on the wearer's chest and that includes a chin support, wherein the strap is removably attached to the front piece.

15. The collar of claim 14 wherein the strap is removably attached using a hook and loop fastener.

16. The collar of claim 6, wherein the back panel is fully removable from other portions of the collar, and can lie substantially flat.

17. A cervical collar that can be positioned about a wearer's neck, comprising:
    a back panel having a top and a bottom, wherein a tab is coupled to the back panel and located intermediate between the top and the bottom, and wherein the tab extends anteriorly to press against a posterior portion of the wearer's neck to thereby promote a cervical curvature; and a support member coupled to the back panel, wherein the support member has a support tab that coincides at least partially with the tab of the back panel.

18. A cervical collar that can be positioned about a wearer's neck, comprising:

a back panel having a top and a bottom, and defining an opening intermediate between the top and the bottom;

a tab having a portion movable within the opening that presses anteriorly against the wearer's neck to thereby promote a cervical curvature;

a front panel; and a connecting strap that couples the front and back panel, wherein the strap overlies a portion of the tab.

19. The collar of claim 18 wherein the tab extends downwardly towards the bottom.

* * * * *